United States Patent
Carmel et al.

(10) Patent No.: US 6,921,399 B2
(45) Date of Patent: Jul. 26, 2005

(54) HIGH EFFICIENCY ELECTROSURGERY PROBE

(75) Inventors: Yuval Carmel, Rockville, MD (US); Anatoly Shkvarunets, Rockville, MD (US)

(73) Assignee: Electrosurgery Associates, LLC, Rockville, MD (US)

( * ) Notice: Subject to any disclaimer, the term of this patent is extended or adjusted under 35 U.S.C. 154(b) by 75 days.

(21) Appl. No.: 10/226,280

(22) Filed: Aug. 23, 2002

(65) Prior Publication Data

US 2003/0088243 A1 May 8, 2003

Related U.S. Application Data

(60) Provisional application No. 60/330,918, filed on Nov. 2, 2001.

(51) Int. Cl.[7] .................................. A61B 18/14
(52) U.S. Cl. ............................. 606/41; 606/45
(58) Field of Search ................ 606/41, 45, 47, 606/49

(56) References Cited

U.S. PATENT DOCUMENTS

| | | | | |
|---|---|---|---|---|
| 4,844,099 A | * | 7/1989 | Skalsky et al. | 607/120 |
| 6,066,134 A | * | 5/2000 | Eggers et al. | 606/32 |
| 6,102,046 A | * | 8/2000 | Weinstein et al. | 128/898 |

* cited by examiner

Primary Examiner—Linda C. M. Dvorak
Assistant Examiner—Aaron Roane
(74) Attorney, Agent, or Firm—Dickstein Shapiro Morin & Oshinsky LLP

(57) ABSTRACT

A high efficiency electrosurgical electrode with an advanced metallic tip and insulator design, and a method of conducting an electrosurgical procedure with such electrode are disclosed. The electrosurgical electrode comprises a metallic body portion of various geometries, a metallic tip and a dielectric insulator adjacent the metallic body portion. The metallic tip comprises a plurality of metallic protuberances of various forms and geometries, which are separated by a plurality of grooves, also of various geometries. The plurality of grooves may be filled with a dielectric material to form various flat dielectric regions surrounding the plurality of metallic protuberances.

14 Claims, 8 Drawing Sheets

HIGH EFFICIENCY ELECTROSURGERY PROBE

The present application claims the benefit under 35 U.S.C. 119(e) of U.S. Provisional Application Ser. No. 60/330,918 filed on Nov. 2, 2001, the disclosure of which is incorporated by reference herein.

FIELD OF THE INVENTION

The present invention relates to the field of electrosurgery and, in particular, to electrosurgical devices and methods which employ high frequency voltage to cut, ablate or coagulate tissue in a fluid environment.

BACKGROUND OF THE INVENTION

Electrosurgical procedures typically rely on the application of very high frequency or radio frequency (RF) electrical power to cut, ablate or coagulate tissue structures. For example, electrosurgery cutting entails heating tissue cells so rapidly that they explode into steam leaving a cavity in the cell matrix. When the electrode is moved and fresh tissue is contacted, new cells explode and the incisions is made. Such electrosurgical cutting involves the sparking of the current to the tissue, also known as the jumping of the RF current across an air gap to the tissue.

Radiofrequency electrodes employed in electrosurgical procedures are generally divided into two categories: monopolar devices and bipolar devices. In monopolar electrosurgical devices, the RF current generally flows from an exposed active electrode through the patient's body, to a passive or return current electrode that is externally attached to a suitable location on the patient's skin. In bipolar electrosurgical device, both the active and the return current electrodes are exposed and are typically in close proximity. The RF current flows from the active electrode to the return electrode through the tissue. Thus, in contrast with the monopolar electrosurgical devices, the return current path for a bipolar device does not pass through the patient's body except for close proximity to the tip of the electrode. Note that bipolar electrosurgical devices are not commonly used in open surgery.

Electrosurgery which takes place in a conductive fluid environment, such as inside of a joint or body cavity filled with, for instance, normalized saline solution, differs from that described previously in that current is conducted from the active electrode through the fluid to the return electrode. In the case of a monopolar device, the current flows through the patient to the return electrode in the manner previously described. In the case of bipolar devices operating in a conductive fluid environment, the return electrode is not in contact with tissue, but rather is submerged in the conductive fluid in the proximity of the active electrode. Current flow is from the active electrode through the conductive liquid and surrounding tissues to the return electrode of the bipolar device. Whether an electrode is monopolar or bipolar, current flows from all uninsulated surfaces of the active electrode to the return electrode anytime that the electrode is energized. This is in contrast to conventional surgery (also called "open surgery") in which current flows only through electrode surfaces in contact with the patient's tissue.

For an electrode in a fluid environment to vaporize tissue, as in the cutting process described previously, the current density at the electrode/tissue interface must be sufficiently high to insulate the electrode through creation of steam bubbles. Voltage of the electrode must be sufficiently high to cause arcing between the electrode and the patient through the steam bubbles. If such current density and voltage are not achieved, power flows from the active electrode to the return electrode with no desirable clinical effect. In fact, such current flow is highly undesirable since the current flowing from the active electrode heats the conductive fluid in the region surrounding the active electrode. A surgeon using a device which is energized but not arcing to the tissue may believe that he is not affecting tissue in close proximity to the active electrode, however, he may be subjecting the tissue to temperatures approaching 100° C. Even when the electrode is arcing to the tissue, the thermal effects are not limited to vaporization of the tissue. Appreciable undesirable heating of the fluid and tissue in the vicinity to the electrode takes place.

One way of avoiding the negative effects of the undesirable heating of the fluid and adjacent tissue structures is to set the power of the electrosurgical generator to a level that is low enough to minimize the heating of the liquid but high enough to produce sparks. There is an inherent difficulty, however, in satisfying acceptable electrosurgical parameters, since virtually all electrosurgical electrodes are "ignited," i.e., generate sparks, only when brought into contact with tissue, and then, generally, after a time delay of varying lengths. At the instant when sparks are not generated, most of the RF power supplied to an electrode operating in a conducting fluid is dissipated in the fluid itself as heat, consequently raising the temperature of the fluid within the joint and the adjacent tissue. At the instant when sparks are generated, the RF power is used for the creation of sparks in the vicinity of the electrodes. Therefore, energizing the electrosurgical electrode without initiation of sparks is dangerous and undesirable, as the heating may damage tissue structure uncontrollably in surrounding areas and also deep under the surface.

During the past several years, specialized arthroscopic electrosurgical electrodes also called ablators have been developed for arthroscopic surgery. The ablator electrodes differ from the conventional arthroscopic electrosurgical electrodes in that they are designed for the bulk removal of tissue by vaporization, rather than by cutting the tissue or coagulating the bleeding vessels. This way, during ablation, volumes of tissue are vaporized rather then discretely cut out and removed from the surgical site.

The power requirements of ablator electrodes are generally higher than those of other arthroscopic electrodes. The efficiency of the electrode design and the characteristics of the radio frequency (RF) power supplied to the electrode also affect the amount of power required for ablation. For example, electrodes with inefficient designs and/or powered by RF energy with poorly suited characteristics will require higher powers levels than those with efficient designs and appropriate generators. Probes used in electrosurgery have relatively large area of metallic electrode, which is the active area of the probe. Large electrode area decreases the probe impedance and, therefore, increases the RF power required for proper operation. The shape of the dielectric insulator and of the electrode tip can significantly affect ablation by bubble and spark formation. By properly shaping the insulator and the electrode tip, the threshold power can be substantially decreased.

The amount of fluid temperature increase within a joint and, consequently, the temperature of the adjacent tissue is critical during the use of ablator electrodes. The fluid temperature may easily reach 45° C., at which cell death typically occurs, and this temperature is easily reached with high-powered ablators operating when sufficient flow is not used. The increase in the fluid temperature is also directly proportional to the increase in the power level. As such, the fluid temperature increases as the period of time necessary for an electrosurgical ablator to be energized increases. Standard arthroscopic electrosurgical electrodes are generally energized for only brief periods (generally measured in seconds) while specific tissue is resected or modified. In contrast, ablator electrodes are energized for longer periods of time (often measured in minutes) while volumes of tissue are vaporized.

During ablation, current flow from the ablator into the conductive fluid heats the fluid to its boiling point. Initially, steam bubbles form only at the edges of the ablator, but eventually they cover the entire surface of the electrode. The electrical resistance to current flow increases to its maximum value, maximum voltage is applied to the steam gap and, if the voltage is larger than some critical value, sparking occurs within the bubble. Sparking within the bubble destroys the tissue which is within the same bubble. After the tissue is destroyed, the sparking continues but no beneficial destruction takes place until new tissue is brought into contact with the active region of the probe.

During the time when sparking does not occur, current flow into the fluid during this time causes heating of the fluid with no desirable clinical effect to the patient. Most intensive heating takes place in the region very close to the electrode, where current density is highest. The induced current also heats the liquid and tissue which is a little further away from the immediate vicinity of the electrode tip. This heating is highly undesirable and potentially dangerous as it may damage tissue structure uncontrollably in surrounding areas and also deep under the surface. If higher efficiency probes could be designed, it would lead to less heating of the fluid and it will confer the surgeon a larger safety margin during a specific surgical procedure.

Accordingly, there is a need to minimize the heating of the conductive fluid and especially of the adjacent tissue during an electrosurgical procedure, to achieve improved tissue removal rates at low power levels and to avoid patient burns. There is also a need for an electrosurgical electrode of high efficiency and high impedance with an improved design of the metal electrode tip and of the adjacent dielectric insulator, which is capable of conferring high ablation rates at low RF power levels. A method of fabricating such electrosurgical electrode with advanced electrode tip design and methods of utilizing such electrode in various electrosurgical procedures, are also needed.

BRIEF SUMMARY OF THE INVENTION

In one aspect, the invention provides a high efficiency electrosurgical electrode with an advanced metallic tip and insulator design that achieves high ablation rates at low RF power levels. The electrosurgical electrode comprises a metallic body region of various geometries, a metallic tip and a dielectric insulator adjacent the metallic tip and the metallic body portion. The metallic tip and dielectric material are designed to form a high current density zone for bubble formation at the tip of the electrode and to confer additional insulation to the electrode. According to one embodiment, the metallic tip is provided with a groove having various geometries and dimensions. The groove may be filled with a dielectric material to form a flat dielectric region. The dielectric material of the flat dielectric region may be the same as, or different from, the dielectric insulator adjacent the metallic body portion.

According to another embodiment, the metallic tip comprises a plurality of metallic protuberances of various cross-sections and/or geometries and which are spaced from each other by a predetermined distance and are separated by a plurality of grooves having various geometries and dimensions. The grooves may be filled with a dielectric material to form various flat dielectric regions. The dielectric material of the flat dielectric regions may be the same as, or different from, the dielectric insulator adjacent the metallic body portion.

In another aspect, the invention provides an apparatus for conducting electrosurgical procedures or interventions comprising at least one electrosurgical probe that includes a shaft having a proximal end and a distal end. The distal end supports at least one electrosurgical electrode comprising a metallic electrode having a metallic tip. The metallic tip may be provided with at least one groove which may be filled with a dielectric material. Alternatively, the metallic tip may comprise a plurality of metallic protuberances of various geometrical forms that are spaced from each other by a predetermined distance and are surrounded by a plurality of flat dielectric regions. The metallic tip may have its lateral walls at an incidence angle with adjacent dielectric walls of about 10 to 80 degrees, more preferably of about 35 to 55 degrees.

The invention also provides a method of forming an electrosurgical electrode by constructing a metallic electrode so that the metallic tip at the proximal part of the metallic electrode comprises a plurality of metallic protuberances of various shapes and geometries which are spaced apart and surrounded by a plurality of dielectric regions, also of various shapes and geometries. The metallic tip may have lateral walls at an incidence angle with adjacent dielectric walls of about 10 to 80 degrees, more preferably of about 35 to 55 degrees.

The invention also provides a method of employing an electrosurgical electrode in an electrosurgical procedure for which the total time the electrode needs to be in contact with the tissue structure is decreased. The method comprises the steps of: (i) positioning an electrosurgical electrode adjacent a target tissue, the electrosurgical electrode comprising a metallic electrode comprising a plurality of metallic protuberances spaced apart and surrounded by a plurality of dielectric regions, and then (ii) either submerging the target tissue in an electrical conducting fluid or (iii) directing an electrically conducting fluid to the target tissue to allow the formation of a high current density zone for bubble trap and spark formation in the region adjacent the metallic electrode and ablate tissue.

These and other features and advantages of the invention will be more apparent from the following detailed description that is provided in connection with the accompanying drawings and illustrated exemplary embodiments of the invention.

DETAILED DESCRIPTION OF THE PREFERRED EMBODIMENTS

The present invention provides an electrosurgical probe with an electrosurgical electrode having an advanced insulator and metallic tip design and being capable of achieving high ablation rates at low RF power supply. As described in more detail below, the present invention contemplates the use of a single active electrosurgical electrode or of an array of such active electrosurgical electrodes uniformly distributed over a distal surface of an electrosurgical probe.

Figure 1:
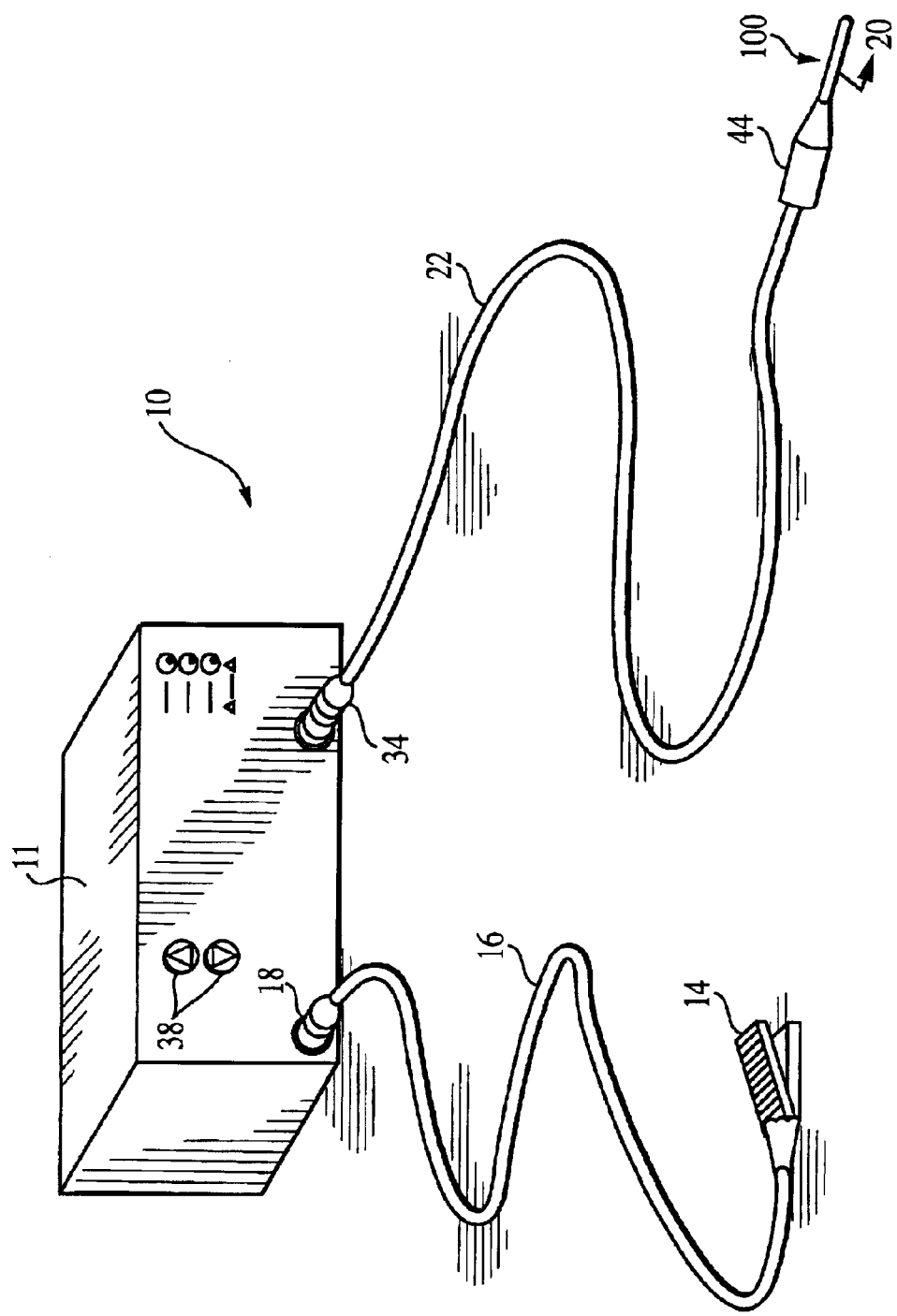
FIG. 1 is a perspective view of an electrosurgical system which includes an electrosurgical electrode of the present invention.

Referring now to the drawings, where like elements are designated by like reference numerals, FIG. 1 illustrates a monopolar electrosurgical system 10 that employs a monopolar electrosurgical probe 20 of the present invention. The monopolar electrosurgical system 10 of FIG. 1 may be used, for example, in the treatment of body tissue in minimally invasive procedures within the body, for example, in procedures that require the introduction of a surgical instrument through a percutaneous penetration or through a natural opening in the patient. Although, for simplicity, the invention will be described below with reference to a monopolar electrode, such as the monopolar electrosurgical electrode 100 (FIG. 2), the invention has equal applicability to systems employing bipolar electrosurgical electrodes.

As illustrated in FIG. 1, the monopolar electrosurgical system 10 includes an electrosurgical probe 20 that is connected to receptacle 34 of the electrosurgical power supply 11 by conductor cable 22. The electrosurgical probe 20 comprises a connector housing 44 at its proximal end, and an electrosurgical electrode 100 at its distal end. Power supply 11 provides very high frequency or radio frequency (RF) voltage to the electrosurgical electrode 100. Power supply 11 is also provided with an operator-controllable voltage level adjustment 38 to control the applied voltage level. Thus, a surgeon or a medical operator may manually adjust the voltage level applied to electrosurgical electrode 100 through voltage level adjustment 38.

Power supply 11 of FIG. 1 also includes a foot pedal 14 which may be removably coupled to receptacle 18 through cable connector 16. The foot pedal 14 may be used to place the power supply into a predetermined operation mode, for example, into an "ablation" mode or a "coagulation" mode. In the "ablation" mode, a sufficient voltage is applied to the electrosurgical electrode 100 through voltage level adjustment 38 so that in ablation mode, a voltage is applied to the electrosurgical electrode 100 through voltage level adjustment 38 so that fluid in at least a portion of the active electrode is vaporized and arcing occurs within the bubbles. The requisite voltage level depends on the characteristics of the electrode and of the RF power supplied to the electrode.

Figure 2:
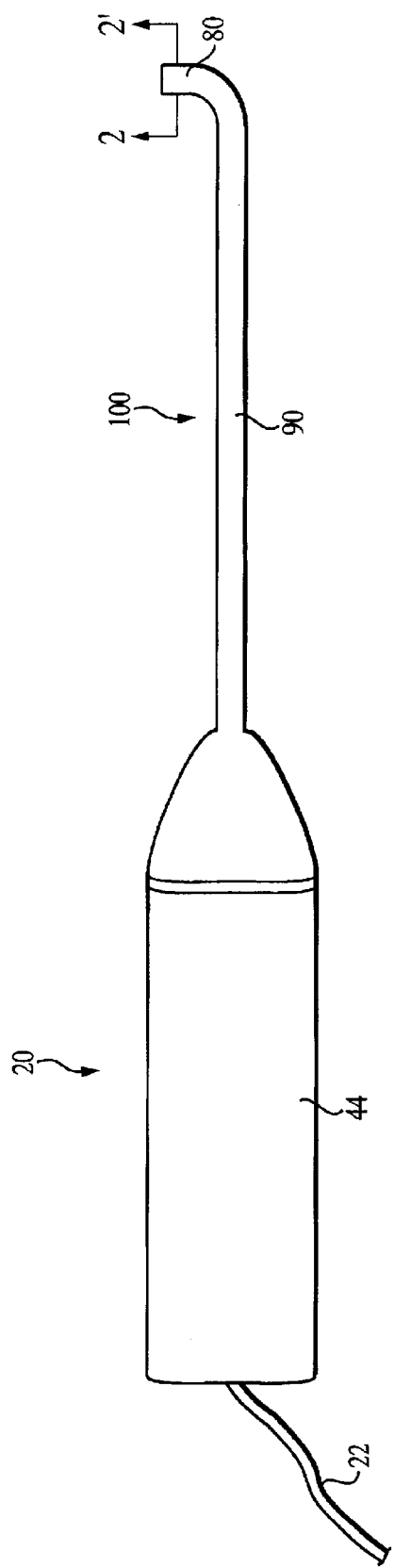
FIG. 2 is a perspective view of the electrosurgical electrode of FIG. 1.

The electrosurgical electrode 100 of FIG. 1 is illustrated in more detail in FIG. 2. The electrosurgical electrode 100 comprises an elongated distal shaft 90 having a proximal end adjacent the connector housing 44, and a distal end in contact with or near a distal active electrode 80. The elongated distal shaft 90 may have a variety of configurations for mechanically supporting the distal active electrode 80 and permitting a treating physician to manipulate the distal active electrode 80 from a proximal end of the shaft. As such, the elongated distal shaft 90 may be a tube or a narrow-diameter rod of dimensions that permit the distal active electrode 80 to be introduced through an associated cannula in a minimally invasive procedure, such as arthroscopic or other endoscopic procedures, or into a body cavity, such as the mouth or the abdominal cavity.

The elongated distal shaft 90 may have a length of about at least 10 cm, more preferably of about 10 to about 100 cm, and a diameter of at least 1 mm, more preferably of about 2 to 10 mm. The elongated distal shaft 90 may be flexible or rigid, or may be formed as a combination of a flexible shaft combined with a generally rigid external tube for increased mechanical and physical support. The elongated distal shaft 90 may also include pull wires or shape memory actuators or other known mechanisms for facilitating the positioning of the distal active electrode 80 in the vicinity of the target tissue. In addition, the elongated distal shaft 90 may include other conductive elements and wires that run axially through the shaft and permit connection of the distal active electrode 80 to a connector at the proximal end of the elongated distal shaft 90.

Various embodiments of the distal active electrode 80 (FIG. 2) of the electrosurgical electrode 100 of the present invention are illustrated in more detail in FIGS. 3–10. Although, for simplicity, the embodiments of the present invention will be described below with reference to only one distal active electrode 80 as part of the electrosurgical electrode 100, the invention is not limited to this exemplary embodiment. Accordingly, the invention also contemplates the formation of a plurality of such distal active electrode 80 as part of an electrosurgical electrode.

Figure 3:
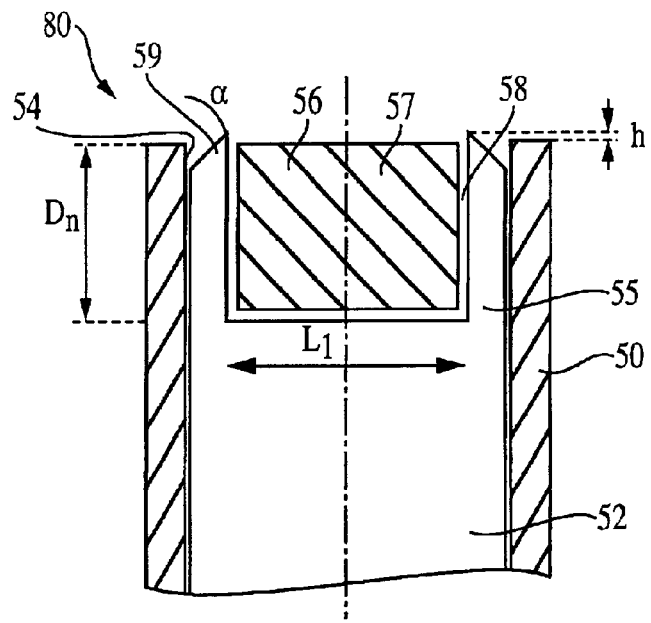
FIG. 3 is an enlarged cross-sectional view of the electrosurgical electrode of FIG. 2 taken along line 2–2' and in accordance with a first embodiment of the present invention.

Referring now to FIG. 3 and in accordance with a first embodiment of the present invention, the distal active electrode 80 of the electrosurgical electrode 100 comprises a dielectric material 50, a metallic body region 52 adjacent the dielectric material 50, and a metallic tip 55 located at the distal end of the metallic region 52.

The dielectric material 50 may comprise an electrically insulating material such as epoxy, plastic, silicon-based material, ceramic, glass or compositions of these mentioned materials, among many others. The dielectric material 50 may also comprise a perforated shield (not shown) also formed of an electrically insulating material which may be porous and which may include an opening that allows an electrically conductive liquid, for example an isotonic saline solution, to contact the metallic tip 55 and the target tissue. The dielectric material 50 covers and insulates the metallic body region 52 and the metallic tip 55. The metallic body region 52 may have various cross-sectional shapes and geometries, for example, cylindrical, rectangular, or elipsoidal, among many others.

The metallic body region 52 and the metallic tip 55 located at the distal end of the metallic region 52 may be formed of electrically conductive materials such as metals and metal alloys, for example, stainless steel and stainless steel alloys, platinum and platinum alloys, gold and gold alloys, nickel and nickel alloys, titanium and titanium alloys, and molybdenum and molybdenum alloys, among others. Sufficient clearance exists between the inner surface of dielectric material 50 and outer surface of metallic body region 52 to allow thermal expansion of the metallic body without cracking the dielectric material, particularly at the distal end of these items. The metallic body region 52 may be bonded to the dielectric material 50 by a sealing material (not shown) which is typically an inorganic sealing material that provides effective electrical insulation and good adhesion to both the dielectric material 50 and the metallic body region 52. The sealing material may preferably have a compatible thermal expansion coefficient and a melting point above the temperature reached in the region during use.

As also illustrated in FIG. 3, the metallic tip 55 is provided with a groove 53 filled with a dielectric material to form dielectric region 57. The groove 53 and the respective dielectric region 57 formed within the groove 53 may have various geometries and/or shapes and various cross-sections, for example, a rectangular cross-section as shown in FIG. 3, or trapezoidal, triangular, square, hexagonal, round, elipsoidal, among many others. The groove 53 and the dielectric region 57 may have a depth "$D_1$" (FIG. 3) of about 1 to about 5 millimeters, more preferably of about 2 millimeters, and a length "$L_1$" (FIG. 3) of about 3 to about 7 millimeters, more preferably of about 5 millimeters.

The dielectric insulator material that fills the groove 53 may be formed of an electrically insulating material such as epoxy, plastic, silicon-based material, ceramic, glass or compositions of these mentioned materials, among many others. Preferably, the dielectric insulator material of the dielectric region 57 is of the same material to that forming the dielectric material 50. However, the invention also contemplates embodiments in which the dielectric insulator material 57 is different from the dielectric material 50. Although contact surface 56 of the dielectric insulator material 57 is illustrated in FIG. 3 as a planar surface, the geometry of this contact surface may vary, primarily according to the location of the target tissue to be treated. Thus, contact surface 56 may be also concave, convex, hemispherical or conical, among many others. Again, sufficient clearance must exist between the inner surface of the groove 53 and outer surface of dielectric region 57 to allow thermal expansion of the metal without cracking the dielectric material.

Figure 4:
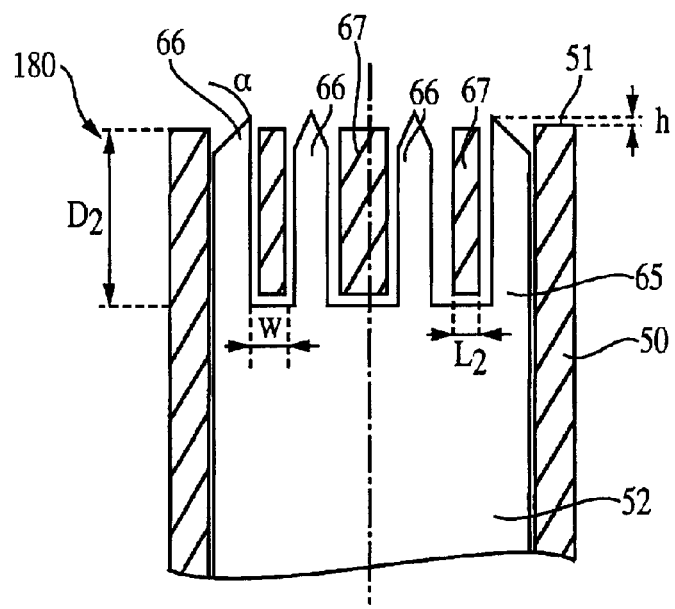
FIG. 4 is an enlarged cross-sectional view of the electrosurgical electrode of FIG. 2 taken along line 2–2' and in accordance with a second embodiment of the present invention.

FIG. 4 illustrates a second embodiment of the present invention according to which distal active electrode 180 of electrosurgical electrode 100 comprises a metallic body region 52 adjacent a metallic tip 65 having a plurality of metallic protuberances or "teeth" 66 spaced apart from each other and surrounded by a plurality of dielectric regions 67. The metallic protuberances or "teeth" 66 may have various geometrical shapes and are spaced from each other by a predetermined distance "w" (FIG. 4) of about 0.1 to about 2 millimeters, more preferably of about 1 to about 2 millimeters. For example, the metallic protuberances 66 of FIG. 4 are illustrated as having a rectangular shape with a triangular area located above transversal distal dielectric surface 51 (FIG. 4) of the dielectric material 50, but other geometries are possible, for example, trapezoidal shape, among others. The plurality of dielectric regions 67 are also illustrated in FIG. 4 as having a rectangular shape with dimensions "$L_2$" of about 1 to 2 millimeters and "$D_2$" of about 2 to 3 millimeters but, again, the dielectric regions 67 may have various geometries and shapes, as desired. As in the first embodiment, the dielectric regions 67 are preferably planar, but the geometry of their contact surface may vary also according to the location of the target tissue to be treated. The dielectric insulator material that forms the dielectric regions 67 may be an electrically insulating material such as epoxy, plastic, silicon-based material, ceramic, glass or compositions of these mentioned materials, among many others. The dielectric insulator material of the dielectric region 67 may be similar to, or different from, the dielectric material 50.

Figure 5A:
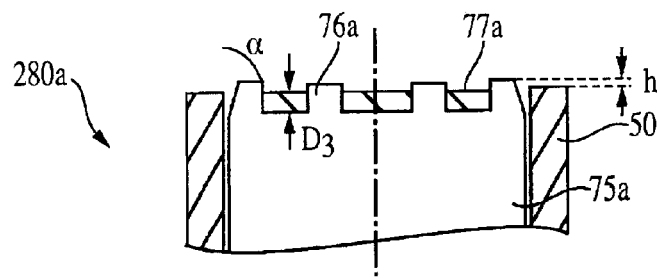
FIGS. 5(a)–(d) are enlarged cross-sectional views of the electrosurgical electrode of FIG. 2 taken along line 2–2' and in accordance with a third embodiment of the present invention.
Figure 5B:
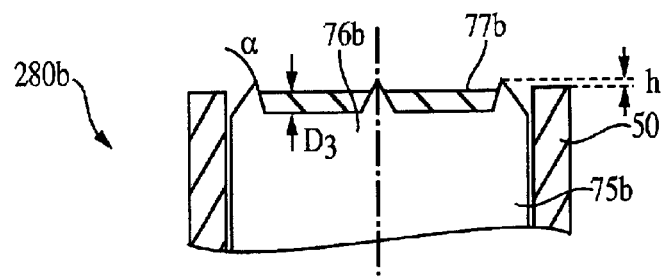
Figure 5C:
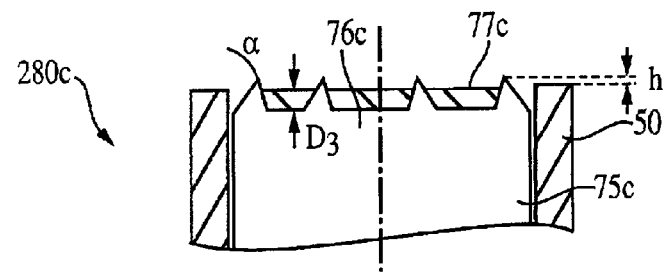
Figure 5D:
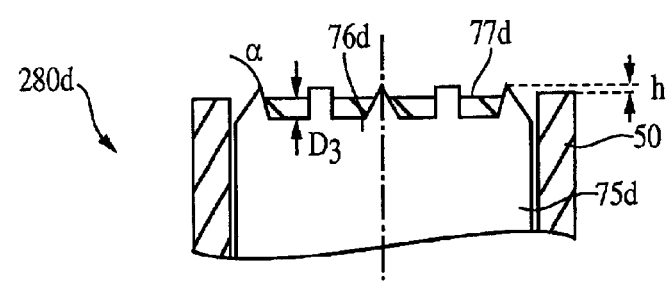

FIGS. 5(a)–(d) illustrate a third embodiment of the present invention, according to which distal active electrodes 280(a)–(d) of the electrosurgical electrode 100 comprise metallic tips 75(a)–(d) having a plurality of metallic protuberances 76(a)–(d) with various configurations, for example, triangular (FIGS. 5(b)–(c)), rectangular (FIG. 5(a)) or a combination of the two (FIG. 5(d)). As shown in FIGS. 5(a)–(d), dielectric regions 77(a)–(d) have a depth "$D_3$" of about 0.1 to about 2 millimeters and various configurations, also according to the configuration of the metallic protuberances 76(a)–(d). Again, the dielectric insulator material that forms the dielectric regions 77(a)–(D) may be formed of an electrically insulating material such as epoxy, plastic, silicon-based material, ceramic, glass or compositions of these mentioned materials, among many others. The dielectric insulator material of the dielectric regions 77(a)–(d) may be the same as, or different from, the dielectric material 50.

In all embodiments described above with respect to FIGS. 3, 4 and 5(a)–(d), the metallic tip of the electrosurgical electrode 100 is shaped so that lateral walls of the metallic tip form an incidence angle "α" (FIGS. 3–5) with adjacent interior dielectric walls. For example, referring to FIG. 3, lateral walls 59 of the metallic tip 55 and dielectric walls 54 of the dielectric material 50 form angle "α" of about 10 to 80 degrees, more preferably of about 35 to 55 degrees. In addition, in all embodiments described above and illustrated with respect to FIGS. 3, 4 and 5(a)–(d), the most distal point of the metallic protuberances extends above the most distal transversal surface 51 (FIG. 4, for example) of the dielectric material 50 by a distance "h" of about 0.1 to 0.5 millimeters.

Figure 6:
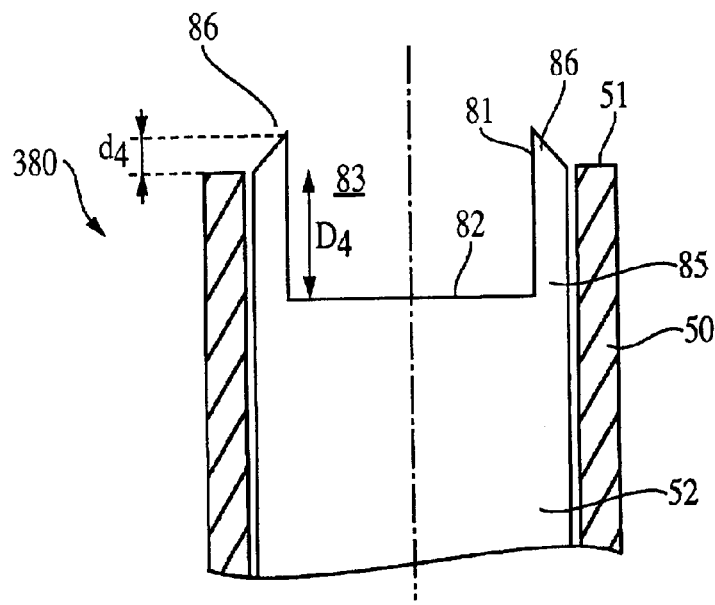
FIG. 6 is an enlarged cross-sectional view of the electrosurgical electrode of FIG. 2 taken along line 2–2' and in accordance with a fourth embodiment of the present invention.

FIG. 6 illustrates yet a fourth embodiment of the present invention, according to which active electrode 380 comprises a metallic tip 85 provided with a groove 83, which is similar in part to the FIG. 3 embodiment, the difference being that the groove 83 of the fourth embodiment is not filled with a dielectric material, as in the previous embodiments. As shown in FIG. 6, the metallic tip 85 is recessed to a distance "$D_4$" from the transversal distal dielectric surface 51 (FIG. 6) to form sidewalls 81 and bottom 82 of the groove 83. The distance $D_4$ may be about 0.1 to about 5 millimeters, more preferably about 3 millimeters. As also illustrated in FIG. 6, the metallic tip 85 is provided with regions 86 which protrude above the transversal distal dielectric surface 51 by a distance "$d_4$" of about 0.1 to about 2 millimeters, more preferably about 0.3 millimeter. Regions 86 of the metallic tip 85 may have various configurations and geometries, the triangular shape of FIG. 6 being just one exemplary embodiment.

Figure 7:
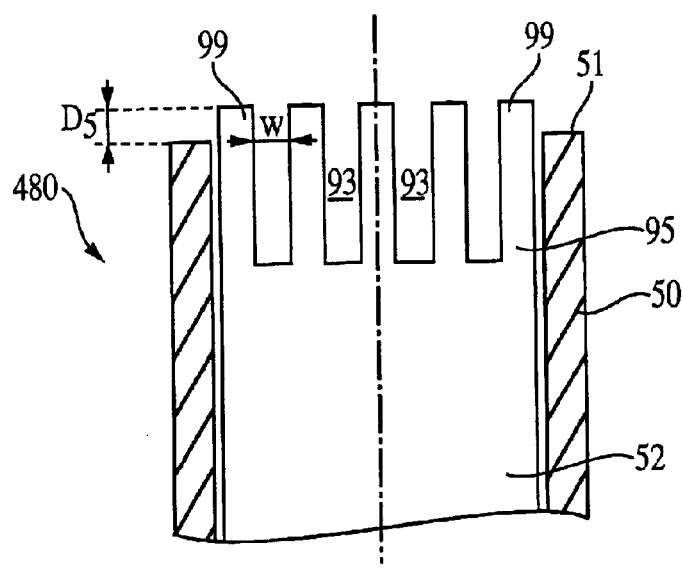
FIG. 7 is an enlarged cross-sectional view of the electrosurgical electrode of FIG. 2 taken along line 2–2' and in accordance with a fifth embodiment of the present invention.
Figure 8A:
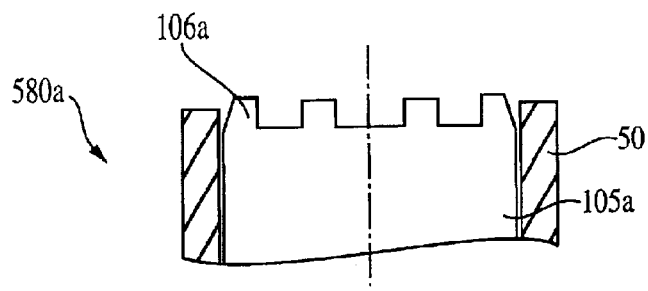
FIGS. 8(a)–(d) are enlarged cross-sectional views of the electrosurgical electrode of FIG. 2 taken along line 2–2' and in accordance with a sixth embodiment of the present invention.
Figure 8B:
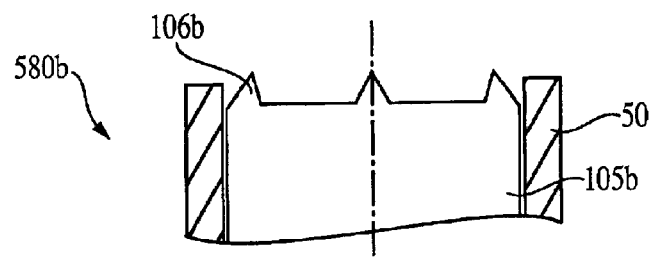
Figure 8C:
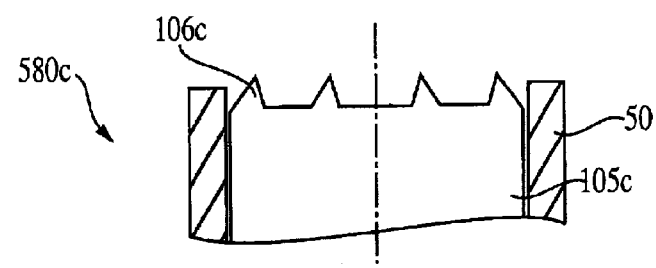
Figure 8D:
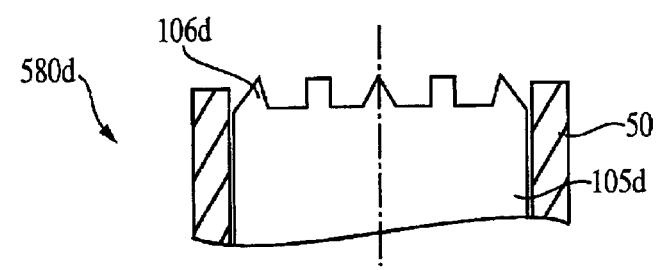

FIG. 7 illustrates another embodiment of the present invention which is similar in part to the embodiment of the FIG. 4 structure to the extent that metallic tip 95 of electrosurgical electrode 480 comprises a plurality of metallic protuberances or "teeth" 99 spaced from each other by distance "w" (FIG. 7) of about 0.1 to about 2 millimeters, more preferably of about 1 to about 2 millimeters. However, the metallic protuberances or "teeth" 99 are not surrounded by a dielectric region or a plurality of dielectric regions, as in the previously described embodiments, but are rather spaced from each other and surrounded by a plurality of grooves 93 (FIG. 7) which are not filled with any material. The metallic protuberances 99 of FIG. 7 are illustrated as having a rectangular shape, but may other geometries are possible, for example, trapezoidal shape, among others. As also shown in FIG. 7, metallic protuberances or "teeth" 99 protrude above the most distal transversal dielectric surface 51 by a distance "$D_5$". The distance $D_5$ may be about 0.1 to about 5 millimeters, more preferably about 0.3 millimeters.

FIGS. 8(a)–(d) illustrate additional embodiments of the present invention, which are similar in part to those described and illustrated above with reference to FIGS. 8(a)–(d) to the extent that the metallic tips 105(a)–(d) of FIGS. 8(a)–(d) comprise a plurality of metallic protuberances or "teeth" 106(a)–(d) which are similar to the metallic protuberances or "teeth" 76(a)–(d) of the FIGS. 5(a)–(d) embodiment, but without the dielectric regions separating and surrounding such metallic protuberances. Again, the metallic protuberances 106(a)–(d) may have various configurations such as rectangular, triangular or circular, among many others.

Figure 9:
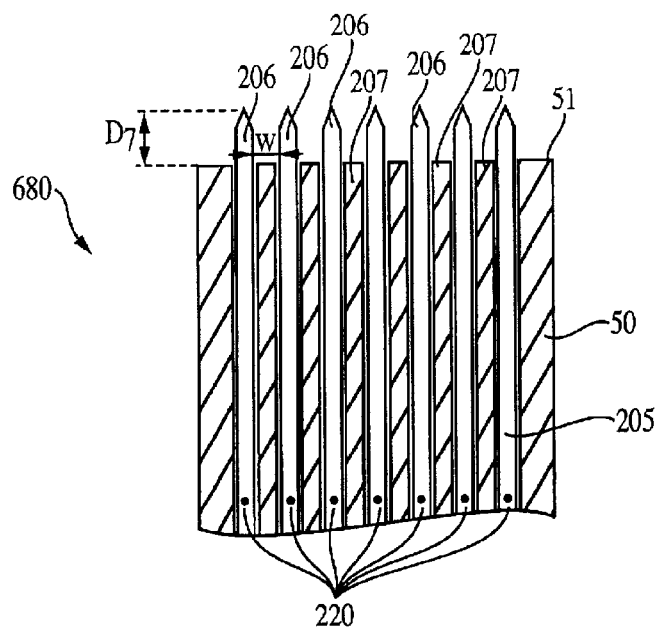
FIG. 9 is an enlarged cross-sectional view of the electrosurgical electrode of FIG. 2 taken along line 2–2' and in accordance with a seventh embodiment of the present invention.
Figure 10A:
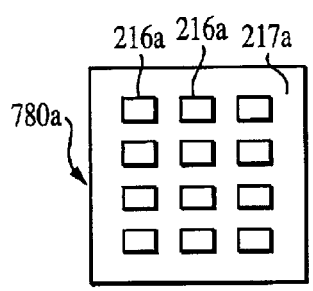
FIGS. 10(a)–(e) are top views of the electrosurgical electrode of FIG. 9.
Figure 10B:
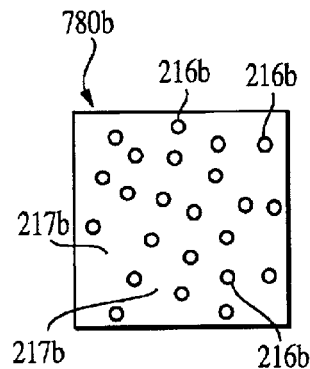
Figure 10C:
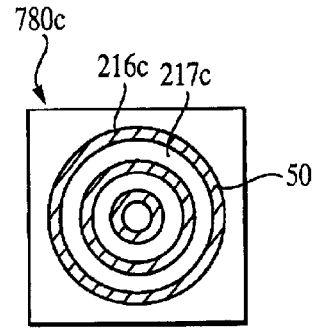
Figure 10D:
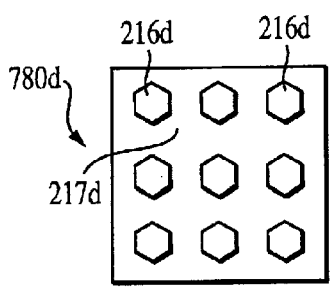
Figure 10E:
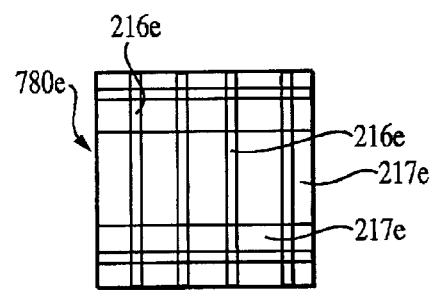

FIG. 9 illustrates yet another embodiment of the present invention according to which metallic tip 205 of distal active electrode 680 (FIG. 9) of the electrosurgical electrode 100 comprises a plurality of elongated metallic protuberances 206 spaced apart from each other by distance "w" (FIG. 9) and surrounded by a plurality of flat dielectric regions 207. The plurality of elongated metallic protuberances 206 of the metallic tip 205 may all converge to a wire connection 220, as shown in FIG. 9. As in the FIG. 7 embodiment, the metallic elongated protuberances 206 of the electrosurgical electrode 680 protrude above the most distal transversal dielectric surface 51 by a distance "$D_7$." The distance $D_7$ may be about 0.1 to about 5 millimeters, more preferably about 0.3 millimeters. The distance "w" (FIG. 9) is of about 0.1 to about 2 millimeters, more preferably about 1 to about 2 millimeters.

The metallic protuberances 206 are illustrated in FIG. 9 as having a combined rectangular and triangular shape, but it must be understood that many other geometries are possible, for example, rectangular, circular or trapezoidal shape, among many others. For example, FIGS. 10(a)–(e) illustrate active electrodes 780(a)–(e) having metallic protuberances 216(a)–(e) of various cross-sections and surrounded by dielectric regions 217(a)–(e), respectively.

As a result of the improved design of the metallic tip and surrounding dielectric material, the electrosurgical electrode 100 of the present invention, which was illustrated and described above with reference to FIGS. 1–10, operates effectively at low RF power when the electrosurgical electrode 100 is brought in contact with a tissue. The high efficiency electrode 100 of the present invention has a decreased metallic electrode area, which leads to a substantial increase in the probe impedance. In addition, the shape of the metallic protuberances, for example the metallic protuberances 99 of FIG. 7, generate grooves in the metallic electrode, such as grooves 93 of FIG. 7, which increase the electrode area for trapping heated liquid and generating bubble and spark formation when the electrosurgical electrode 100 is brought in contact with a tissue to be treated. Thus, as a result of the increased ability to trap bubbles and generate sparks at the tip of the metallic electrode, less power is needed to create bubbles than in a conventional probe.

Increasing the impedance of the electrosurgical electrode 100 and the ability to trap steam bubbles further reduces the ignition problems associated with conventional electrosurgical electrodes, therefore making the operation of the electrosurgical electrode 100 more controlled. Since the necessary RF power is smaller than that of a conventional probe, a surgeon conducting a procedure employing the electrosurgical electrode 100 of the present invention has a larger margin of safety, which in turn reduces the chances of patient burns. The contact time between the electrosurgical electrode 100 of the present invention and the tissue to be treated is also decreased.

The high efficiency electrosurgical electrode 100 of the present invention illustrated and described above with reference to FIGS. 1–10 may be employed in a variety of surgical medical procedures in the presence of an electrically conductive fluid to remove and/or modify a particular target tissue. Accordingly, the electrosurgical electrode 100 of the present invention may be used in a conventional open surgery environment or in other, less invasive, techniques that use cannulas or various port access devices if conductive fluid is present. The present invention has also applications in surgical procedures where the target tissue is flooded with, or submerged in, an electrically conductive fluid such as in many arthroscopic procedures for ablation, coagulation, shaping and cutting of various body parts such as the knee, shoulder, hip, ankle, elbow, hand or foot.

The present invention has also equal applicability to surgical procedures where the target tissue is flooded with a natural conductive fluid of the human body, such as blood or lymphatic plasma, for example, which act as electrically conductive fluids. Nevertheless, an electrically conductive fluid introduced into the patient's body is preferred over blood because blood tends to coagulate at certain temperatures. In addition, the patient's blood or plasma may lack the necessary conductivity to adequately carry out the particular electrosurgical procedure desired.

Surgical procedures using the electrosurgical electrode 100 of the invention include introducing the electrode assembly in close proximity to the surgical site through an artificial conduit or a cannula, or through a natural conduit which may be in an anatomical body cavity or space or one created surgically. For the purposes of the present invention, the terms "close proximity" and "proximity" are defined as "in contact with" or "at a distance of about 0.1 to about 10 millimeters." The cavity or space may be distended during the procedure using a fluid or may be naturally held open by anatomical structures. In addition, the surgical site may be bathed in a continuous flow of conductive fluid, such as saline solution, to fill and distend the cavity. The procedures may include simultaneous viewing of the site via an endoscope or using an indirect visualization means.

Figure 11:
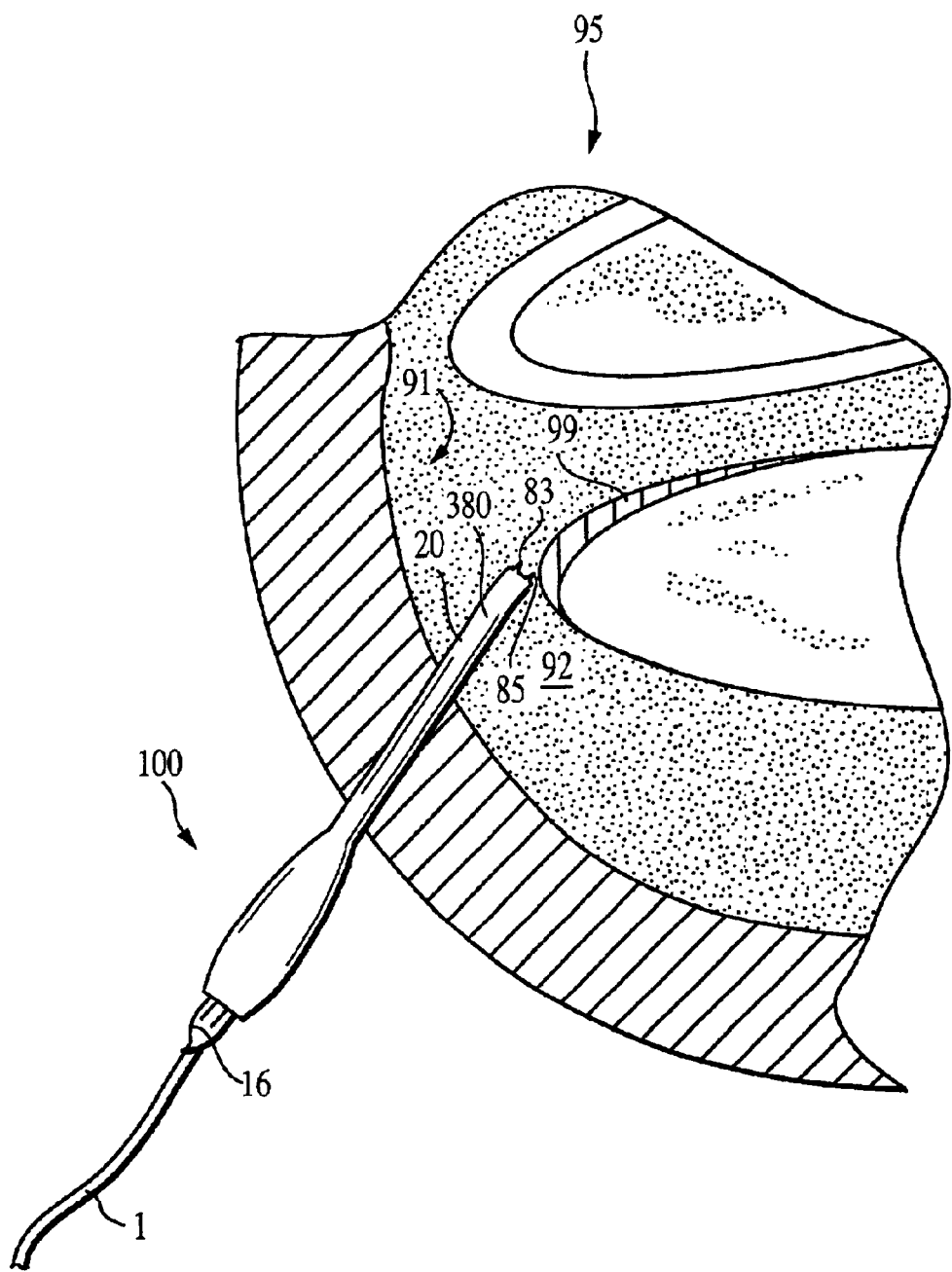
FIG. 11 is a schematic cross-sectional view of a knee joint undergoing an electrosurgical procedure employing an electrosurgical electrode of the present invention.

To better illustrate an exemplary surgical procedure conducted with the electrosurgical electrode 100 of the present invention, reference is now made to FIG. 11, which illustrates a schematic cross-sectional view of a knee joint region 95. The knee joint region 95 of FIG. 11 may undergo an arthroscopic procedure, for example, with electrosurgical probe 20 having electrosurgical electrode 100 and distal active electrode 380 (FIG. 6) fabricated according to the third embodiment of the present invention. As known in the art, an endoscope (not shown) may be provided at one end with the distal active electrode 380, and then introduced into knee cavity 92 (FIG. 11) containing electrically conductive fluid 91 (FIG. 11) and in close proximity to target tissue 99 (FIG. 11). If the target tissue 99 of the knee joint region 95 is a damaged meniscus, for example, then target tissue 99 may undergo a partial or complete electrosurgical meniscectomy using active electrode 380. Alternatively, the endoscope may be introduced separately from the electrosurgical electrode 380, via separate access means in a surgical technique commonly known as triangulation. In any event, knee cavity 92 may be distended during the arthroscopic procedure using electrically conductive fluid 91, so that target tissue 99 may be bathed in a continuous flow of conductive fluid 91, which may be preferably a saline solution.

Once distal active electrode 380 is positioned in the proximity of the target tissue 99 and the target tissue 99 is submerged in the electrically conductive fluid 91, the electrosurgical probe 20 is energized by the electrosurgery power supply 11 (FIG. 1). The power supply delivers radio frequency energy, typically in the range of 100 kHz to 3 MHz, through the cable system 22 (FIGS. 1 and 11) to the electrosurgical electrode 100 and further to the distal active electrode 380.

Although the present invention has been described above with reference to arthroscopic surgery of a knee joint structure, the invention is not limited to the above embodiments. Accordingly, the electrosurgical electrode 100 (FIGS. 1–10) of the invention may be employed for a variety of arthroscopic procedures, for example, in the dissection, resection, vaporization, desiccation and coagulation of tissue structures in various endoscopic and percutaneous procedures performed on joints of the body including, but not limited to, spinal and other non-synovial joint techniques. Arthroscopic procedures encompassed by the present invention may further include: lateral retinacular release of the knee joint; removal of anterior and posterior cruciate ligaments; labral tear resection; acromioplasty, bursectomy and subacromial decompression of the shoulder joint; anterior release of the tempomandibular joint; synovectomy, cartilage debridement, chondroplasty, division of intra-articular adhesions, fracture and tendon debridement as applied to any of the synovial joints of the body; inducing thermal shrinkage of joint capsules as a treatment for recurrent dislocation, subluxation or repetitive stress injury to any articulated joint of the body; discectomy either in the treatment of disc prolapse or as part of a spinal fusion via a posterior or anterior approach to the cervical, thoracic and lumbar spine or any other fibrous joint for similar purposes; excision of diseased tissue and haemostasis, among others.

The electrosurgical electrode 100 (FIGS. 1–10) of the present invention may be also used in hysteroscopic surgical procedures or urological endoscopic (urethroscopy, cystoscopy, ureteroscopy and nephroscopy) and percutaneous interventions. Hysteroscopic procedures may include: removal of submucosal fibroids, polyps and malignant neoplasms; resection of congenital uterine anomalies such as a septum or subseptum; division of synechiae (adhesiolysis); ablation of diseased or hypertrophic endometrial tissue; and haemostasis. Urological procedures may include: electrovaporization of the prostate gland (EVAP) and other similar procedures commonly referred to as transurethral resection of the prostate (TURP) including, but not limited to, interstitial ablation of the prostate gland by a percutaneous or perurethral route whether performed for benign or malignant disease; transurethaal or percutaneous resection of urinary tract tumors; division of strictures as they may arise at the pelviureteric junction (PUJ), ureter, ureteral orifice, bladder neck or urethra; correction of ureterocoele, among others.

The above description and drawings illustrate preferred embodiments which achieve the objects, features and advantages of the present invention. It is not intended that the present invention be limited to the illustrated embodiments. Any modification of the present invention which comes within the spirit and scope of the following claims should be considered part of the present invention.

What is claimed as new and desired to be protected by Letters Patent of the United States is:

1. A monopolar electrosurgical probe for a ablation of tissue immersed in a conductive fluid comprising:
   a shaft having a proximal end and a distal end; and
   at least one active electrode operating at a frequency of about 100 KHz to about 3 MHz for tissue ablation, said active electrode being located at or near said distal end and comprising a metallic body region surrounded by a dielectric material and a metallic tip adjacent said metallic body region, said metallic tip further comprising a plurality of protuberances spaced from each other by a predetermined distance, wherein said plurality of protuberances protrude above a most distal transversal surface of said dielectric material, and wherein lateral walls of at least one of said protuberances from a incidence angle with adjacent lateral of said dielectric material so that a groove is defined by said lateral walls of said at least one of said protuberances and said adjacent lateral walls of said dielectric material surrounding said metallic body region.

2. The electrosurgical probe of claim 1, wherein said plurality of protuberances are surrounded by a plurality of dielectric regions.

3. The electrosurgical probe of claim 2, wherein said plurality of dielectric regions comprise an insulating material which is different from said dielectric material.

4. The electrosurgical probe of claim 2, wherein said plurality of dielectric regions comprise an insulating material which is the same as said dielectric material.

5. The electrosurgical probe of claim 2, wherein said plurality of dielectric regions have a planar distal surface.

6. The electrosurgical probe of claim 1, wherein said predetermined distance is of about 0.1 to about 2 millimeters.

7. The electrosurgical probe of claim 6, wherein said predetermined distance is of about 1 to about 2 millimeters.

8. The electrosurgical probe of claim 1, wherein said plurality of protuberances protrude for about 0.1 to about 5 millimeters.

9. The electrosurgical probe of claim 1, wherein said incidence angle is of about 10 to 80 degrees.

10. The electrosurgical probe of claim 1, wherein said metallic protuberances have a cross-sectional shape selected from the group consisting of rectangular, square, circular, trapezoidal, triangular and hexagonal shape.

11. An electrosurgical system for the electrosurgical ablation of tissue immersed in a conductive fluid comprising:
    a power supply source; and
    means for applying high frequency voltage to a monopolar electrosurgical probe, said electrosurgical probe comprising a shaft having a proximal end and a distal end; and an active electrode operating at a frequency of about 100 KHz to about 3 MHz for tissue ablation, said active electrode being located at or near said distal end and comprising a metallic body region surrounded by a dielectric material and a metallic tip adjacent said metallic body region, said metallic tip further comprising a plurality of protuberances spaced from each other by about 0.1 to about 2 millimeters and surrounded by a plurality of dielectric regions, wherein said plurality of protuberances protrude above a most distal transversal surface of said dielectric material, and wherein lateral walls of at least one of said plurality of protuberances form an incidence angle with adjacent laterals walls of said dielectric material so that a groove is defined by said lateral wall of said at one of said plurality of protuberances and said adjacent lateral walls of said dielectric material surrounding said metallic body region.

12. The electrosurgical system of claim 11, wherein said plurality of dielectric regions have a planar distal surface.

13. The electrosurgical system of claim 11, wherein lateral walls of said metallic tip form an incidence angle of about 10 to 80 degrees with adjacent lateral walls of said dielectric material.

14. The electrosurgical system of claim 11, wherein said plurality of protuberances protrude for about 0.1 to about 5 millimeters.

* * * * *

UNITED STATES PATENT AND TRADEMARK OFFICE
CERTIFICATE OF CORRECTION

PATENT NO. : 6,921,399 B2
DATED : July 26, 2005
INVENTOR(S) : Yuval Carmel et al.

It is certified that error appears in the above-identified patent and that said Letters Patent is hereby corrected as shown below:

Column 12,
Line 27, change "said protuberances from a" to -- said protuberances form an --.

Signed and Sealed this

Seventeenth Day of January, 2006

JON W. DUDAS
*Director of the United States Patent and Trademark Office*